United States Patent [19]

Mulcey et al.

[11] Patent Number: 4,868,398

[45] Date of Patent: Sep. 19, 1989

[54] DEVICE FOR THE REAL TIME MEASUREMENT OF THE CONTENT OF AN AEROSOL IN A GAS

[75] Inventors: Philippe Mulcey, Bures sur Yvette; Michel Pourprix, Montlhery; Patrick Pybot, Bonnelles; Jacques Vendel, Sainte Genevieve des bois, all of France

[73] Assignee: Commissariat a l'Energie Atomique, Paris, France

[21] Appl. No.: 164,056

[22] Filed: Mar. 3, 1988

[30] Foreign Application Priority Data

Mar. 4, 1987 [FR] France ................................. 87 02934

[51] Int. Cl.[4] .......................... G01N 1/22; G01N 21/64
[52] U.S. Cl. ................................ 250/458.1; 250/304; 356/36; 356/37; 356/38
[58] Field of Search ................... 250/304, 461.1, 459.1, 250/458.1; 356/38, 37, 36

[56] References Cited

U.S. PATENT DOCUMENTS

| | | | |
|---|---|---|---|
| 2,721,495 | 3/1952 | Schaefer | 356/37 |
| 3,694,085 | 9/1970 | Rich | 356/37 |
| 4,449,816 | 5/1984 | Kohsaka et al. | 356/37 |

FOREIGN PATENT DOCUMENTS

| | | | |
|---|---|---|---|
| 2713396 | 9/1978 | Fed. Rep. of Germany | 250/458.1 |
| 1422188 | 1/1976 | United Kingdom | |

OTHER PUBLICATIONS

"Séparateurs Aérauliques—Méthode de Mesure de l'Efficacité des Filtres au Moyen d'un Aérosol d'Uranine (Fluorescéine)." Éditée par l'Association Francaise de Normalisation (AFNOR)NF X 44-011 (May 1972).

L. P. Murphy, S. J. Fernandez and B. G. Motes, "Comparison of HEPA Filter Test Methods in Corrosive Environments." 16th DOE Nuclear Air Cleaning Conference 801038 (1980) pp. 67-85.

Virginia A. Marple and Klaus Willeke, "Inertial Impactors: Theory, Design and Use." in: Fine Particles: Aerosol Generation Measurement, Sampling, and Analysis (Benjamin Y. H. Liu, ed.; Academic Press, Inc., New York, 1976) pp. 411-445.

J. Bricard, P. Delattre, G. Madelaine and M. Pourprix, "Detection of Ultra-Fine Particles by Means of a Continuous Flux Condensation Nuclei Counter," in: Fine Particles: Aerosol Generation, Measurement, Sampling, and Analysis (Benjamin Y. H. Liu, ed.; Academic Press, Inc., New York, 1976) pp. 565-580.

James H. Roberts, Vivian P. Kafalenos and Thomas J. Yule, "Characterization of Aerosols Containing Fissionable Elements Using Solid-State Track Recorders." Nuclear Instruments and Methods, vol. 147, No. 1 (Nov. 15, 1977) pp. 83-86.

C. Deprun, H. Gauvin, B. Lagarde and LeBeyec, "Application de la Technique du Jet d'Hélium a l'Identification en Ligne de Nouveaux Noyaux par la Détection de Leurs Rayonnements Gamma." Revue de Physique Appliquée, Vol. 9, No. 5 (Sep. 1974) pp. 895-899.

Patent Abstract of Japan, vol. 10, No. 68, 1986 (Abstract of No. (11) 60-207037) (72) (Kousaka) (43) 10-1-8-85.

J. H. Nash, G. G. Leiter and F. Grimm, "Sampling Device for Liquid Droplets", Rev. Sci. Instrum., vol. 38, No. 1, (Jan. 1967), pp. 73-77.

Primary Examiner—Constantine Hannaher
Attorney, Agent, or Firm—Michael N. Meller

[57] ABSTRACT

The present invention provides a device for the real time measurement of the content of an aerosol in a gas.

The device performs the measurement on the basis of a sample of the gas and comprises enlargement means able to condense on the sampled aerosol, a vapor of a liquid, so as to obtain droplets of a solution of the aerosol in the liquid, impaction means, able to spray droplets onto a support provided for collecting at least one known fraction of these droplets, means for the continuous analysis of the thus collected droplets, said analysis means being specific to the aerosol the content of which is to be measured and able to supply information relative to said content and electronic means for processing the information and able to determine the content on the basis of said information.

9 Claims, 2 Drawing Sheets

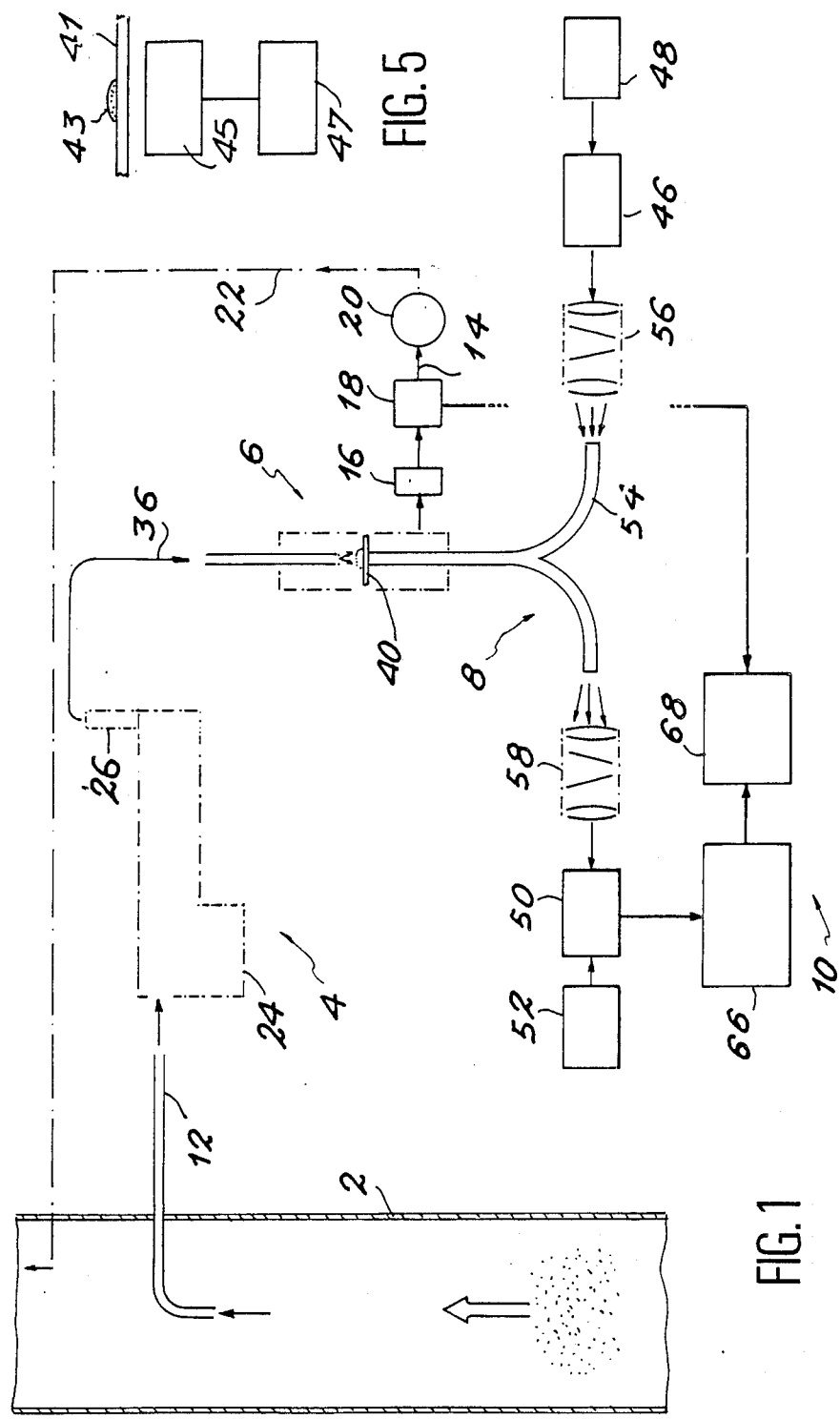

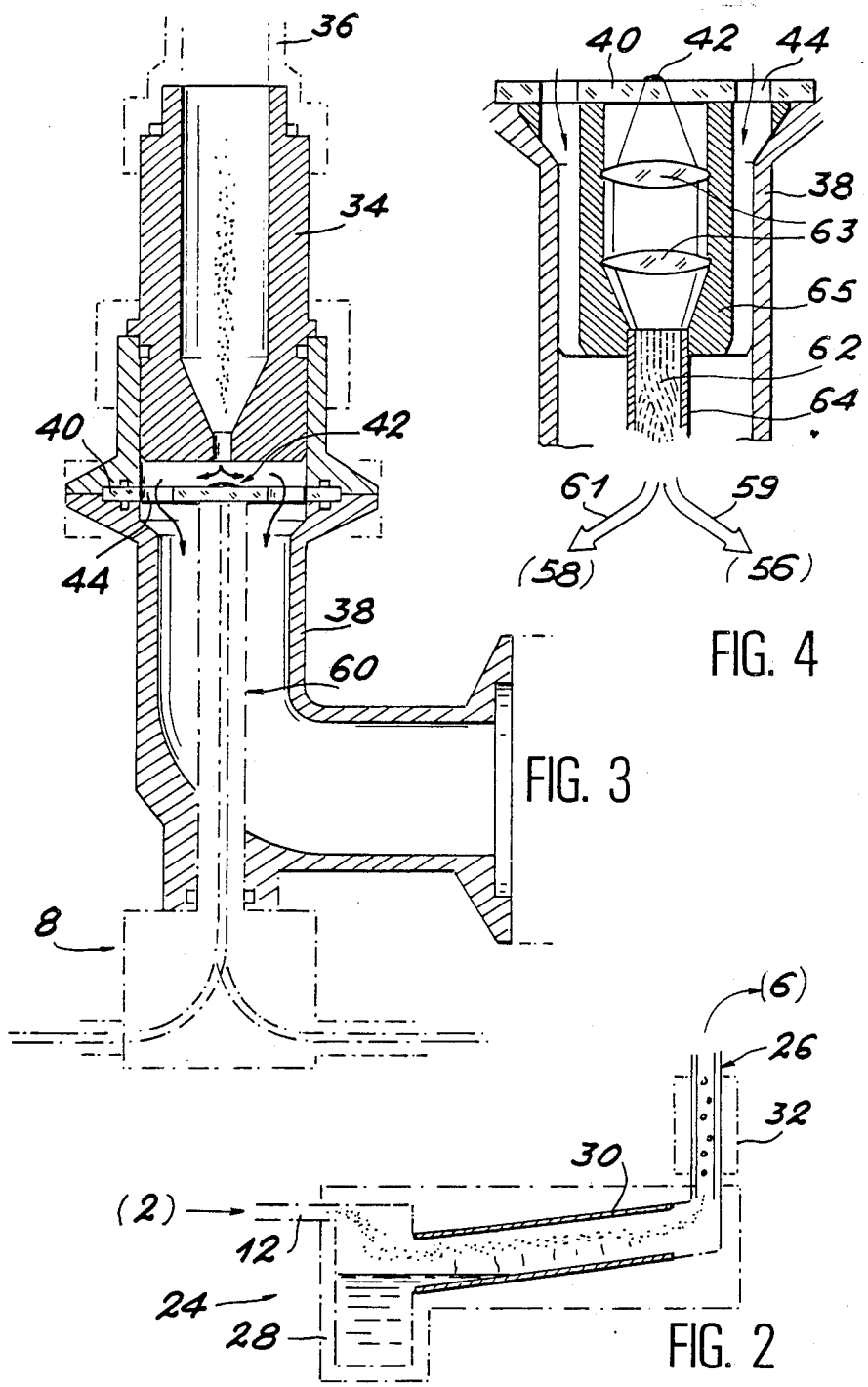

DEVICE FOR THE REAL TIME MEASUREMENT OF THE CONTENT OF AN AEROSOL IN A GAS

DESCRIPTION

The present invention relates to a device for the real time measurement of the content of an aerosol in a gas. It particularly applies to the measurement of the efficiency of filters for aerosols by means of a fluorescent aerosol called "uranin", which is in fact sodium-containing fluorescein of formula $C_{10}H_{20}O_5Na_2$.

A method is already known for measuring the efficiency of filters for aerosols by means of uranin from the following document:

(1) Aeraulic separators—Method for measuring the efficiency of filters by means of a uranin (fluorescein) aerosol. French standard NF-X-44,011—May 1972.

According to this method, with a view to obtaining mass concentrations of uranin upstream and downstream of a filter to be tested, said concentrations being necessary for calculating the efficiency of the filter, the following sequence of operations is performed for the upstream and downstream zones of the filter: collection of the aerosol on a sampling filter for a predetermined time, dissolving the thus collected aerosol in a known volume of an ammoniacal solution of pH 9 and measurement of the fluorescence response of the solution by means of a fluorimeter.

Most specialists in connection with such measurements recongise that uranin has all the "ideal" sought characteristics for a test aerosol, as is indicated in the following document:

(2) L. P. Murphy, S. J. Fernandez, B. G. Motes, Comparison of HEPA filter test methods in corrosive environments—16th DOE Nuclear Air Cleaning Conference. Conf. 801038, 1980 pp. 67 to 85.

However, the aforementioned method suffers from the disadvantage of not permitting a real time measurement and using a single apparatus of the efficiency of the filter for aerosols.

The present invention aims at obviating this disadvantage. The present invention therefore relates to a device for measuring the content of an aerosol in a gas on the basis of a sampling of said gas, characterized in that is comprises enlargement means able to condense on the sampled aerosol, a vapor of a liquid, condense so as to obtain droplets of a solution of the aerosol in the liquid, impaction means, able to spray droplets onto a support provided for collecting at least one known fraction of these droplets, means for the continuous analysis of the thus collected droplets, said analysis means being specific to the aerosol whose content is to be measured and able to supply information relative to said content and electronic means for processing the information and able to determine the content on the basis of said information.

Admittedly, impaction means are already known, particularly from the following document:

(3) Inertial Impactors: Theory, Design and Use, by V. A. Marple and K. Willeke, in Fine particles—aerosol generation, measurement, sampling and analysis—edited by Benjamin Y. H. Liu—Academic Press, Inc., 1976, pp. 411 to 445.

However, these known impaction means are not able to operate with small aerosols (particularly with a size less than approximately 0.5 micrometer). This is rendered possible in the present invention by the unexpected association of impaction means and enlargement means, the function of the latter being to solubilize the aerosol and permit said impaction whilst increasing the inertia of said aerosol.

Enlargement means have already been proposed in order to permit the counting by optical processes of small aerosol particles.

Examples of enlargement means are given in the following documents:

(4) French patent application No. 72222432 of 21.6.1972 and (5) Detection of ultra-fine particles by means of a continuous flux condensation nuclei counter, by J. Bricard, P. Delattre, G. Madelaine, M. Pourprix, in Fine particles—aerosol generation, measurement, sampling and analysis—edited by Benjamin Y. H. Liu—Academic Press, Inc., 1976, pp. 565 to 580.

The means according to the invention cooperate for achieving the sought result, namely the real time measurement of the content of an aerosol in the gas.

The term "real time measurement" is understood to mean on the one hand a measurement, whose result is known at each instant, the duration of the measurement no longer being predetermined, but fixed by the operator who interrupts it when he considers that the accuracy on the result is satisfactory and, on the other hand, a measurement in which the obtaining of the result with the aid of a single apparatus is not deferred by the sequence of operations described hereinbefore.

The present invention also makes it possible to retain all the qualities of the aforementioned method, namely the specificity of the detection with respect to the test aerosol, the use of a spherical, solid and only slightly hygroscopic aerosol usable up to above 150° C., great detection sensitivity and the obtaining of a mass response.

According to a special embodiment of the device according to the invention, the aerosol is fluorescent and the analysis means incorporate optoelectronic fluorescence detection and exciting means able to supply the information.

In a particular realization, the optoelectronic means incorporate:

means for forming a fluorescence exciting light beam, means for detecting a fluorescent light resulting from the excitation and fiber optics means able to transmit the exciting beam to the droplets collected and to transmit the fluorescent light to the detection means.

It is consequently possible to improve the sensitivity of the measurement compared with method described hereinbefore.

Preferably, the support is transparent to the exciting beam and to the fluorescent light, the droplets being collected on one face of the support, the fiber optics means having two groups of optical fibers, each optical fiber having one end placed facing the other face of the support, the ends of the optical fibers placed facing the other face of the support being intermixed and the two groups are respectively provided for transmitting the exciting beam and the fluorescent light.

According to another special embodiment of the device according to the invention, as the aerosol is radioactive and consequently emits alpha, beta or gamma radiation, the analysis means incorporate radiation detection means (nuclear detector) able to supply said information to the associated electronic means. Thus, a measurement takes place of the radioactivity of the aerosol particles deposited on the support, the latter obviously being appropriate for said measurement.

The aerosol can be solid. For example, it can be sodium-containing fluorescein, which is usable in a gas such as air for testing filters for aerosols and as stated hereinbefore.

However, the aerosol entering the device can be liquid. For example it can be dioctyl phthalate (DOP). The considered aerosol can be marked with a fluorescent compound in which it is soluble (e.g. POTOMAK YELLOW in the case of DOP), in order to also use it in a gas such as air for testing filters or aerosols. In this case, use is generally made of a liquid identical to said aerosol for supplying the enlargement means.

The invention is described in greater detail hereinafter relative to non-limitative embodiments and the attached drawings, which show:

FIG. 1 a diagrammatic view of a special embodiment of the device according to the invention.

FIG. 2 a diagrammatic view of the enlargement means used in the device of FIG. 1.

FIG. 3 a diagrammatic view of the impaction means used in said device and of the fiber optics means usable with said impaction means.

FIG. 4 a diagrammatic view of other fiber optics means usable with said impaction means.

FIG. 5 diagrammatically and partly a device according to the invention adapted to a radioactive aerosol.

FIG. 1 diagrammatically shows a special embodiment of the device according to the invention. This device is, e.g., intended for the real time measurement of the mass concentration of a fluorescent aerosol, such as uranin, in the air circulating in a duct, e.g. a ventilation sleeve 2. The device comprises enlargement means 4, impaction means 6, analysis means 8 and electronic processing means 10.

The device is inserted in a conventional circuit for the exhausting of the air circulating in the duct. The circuit comprises a pipe 12 permitting the extraction of the aerosol-charged air in order to bring said air to the enlargement means 4, a pipe 14 in which circulates the air extracted from the impaction means 6 and on which are successively mounted as from the outlet of said impaction means 6, a flow regulator 16, a flowmeter 18 and a suction pump 20; and a duct 22 for returning the air extracted from duct 2 into the latter from pump 20.

The enlargement means 4 are of the type described in document (5) above, p.567, paragraph 3 and consist of a saturator 24, followed by a condenser 26 (FIG. 2). Saturator 24 comprises an intake chamber 28, which also serves as a reservoir for the liquid used in the formation of the droplets around the aerosol particles. It is obviously an appropriate liquid chosen as a function of the aerosol.

In an indicative and non-limitative manner, in the case of an aerosol such as uranin, it is possible to use a liquid such as glycerol. It is also possible to use any other liquid, which is preferably only slightly toxic, in which uranin is soluble in an adequate quantity, said liquid being only slightly volatile at ambient temperature and which, under acceptable operating conditions for the enlargement means, is able to produce droplets with diameters at least equal to one micrometer.

The saturator 24 also comprises a duct 30 communicating by one end with the chamber 28. Condenser 26 is a preferably vertical calibrated nozzle in order to prevent losses of droplets by sedimentation, the latter remaining relatively small. The nozzle is generally provided with cooling means 32, such as a Peltier effect generator and which communicates with the other end of duct 30.

The aerosol sampled in the ventilation sleeve 2 passes by means of pipe 12 to saturator 24, in which it is mixed with the vapor of the liquid.

The temperature in condenser 26 and which is below that of the saturator is fixed in such a way that the vapor condenses on each aerosol particle. Thus, this aerosol is transformed into droplets with a given diameter, e.g. of approximately 2 micrometers.

The impaction means or impacter 6 (FIG. 3) has a vertical accelerating nozzle 34, whereof the upper part communicates with the outlet of condenser 26 by a duct 36 and whereof the lower part (accelerating part) is tightly connected to a duct 38, which is itself connected to duct 14.

Facing the lower part of nozzle 34, within said duct 38 is fixed a horizontal support 40 serving as an impaction surface and which is transparent to the radiation used for analyzing droplets and reference will be made to this radiation hereinafter. This support is e.g. constituted by a microscope slide or a plastic strip. If necessary, it could have a cavity for collecting a larger quantity of droplets.

The air charged with droplets which have formed in condenser 26 is consequently accelerated by nozzle 34 and the droplets drop onto support 40, which collects all of them, or a known fraction, which can be determined on the basis of the operating conditions. A deposit 42 of droplets and therefore aerosol consequently progressively forms on the upper surface of support 40.

Openings 44 are provided in support 40 to permit the discharge of the droplet-charged air not collected by support 40. This air, exhausted by pump 20, leaves duct 38 and returns to the ventilation sleeve 2 via duct 22.

The analysis means 8 incorporate a light source 46 for exciting the fluorescence of the uranin collected by support 40. For example, said source is constituted by an ultraviolet radiation lamp supplied by a high voltage source 48.

The analysis means 8 also incorporate a photomultiplier 50 supplied by a high voltage source 52, as well as fiber optics means 54 for transmitting the light emitted by source 46 to deposit 42 and for transmitting the fluorescent light emitted by said deposit excited by the ultraviolet radiation to photomultiplier 50. In the embodiment shown in FIGS. 1 and 3, means 54 are constituted by a Y-optical coupler.

The light from source 46 is injected into a first branch of coupler 54 via a group of lenses and filters 56, said filters making it possible to select the uranin exciting wavelengths.

The fluorescent light emitted by the deposit is transmitted by a second branch of coupler 54 and is supplied to photomultiplier 50 via another group of lenses and filters 58, the lenses of said other group 58 ensuring that radiation other than the fluorescent light does not reach photomultiplier 50.

The third branch of coupler 54, protected by a rigid tube 60 traverses duct 38 by a tight passage and the end of said third branch is in contact with the lower face of support 40 facing the area of said support where deposit 42 forms.

In place of a Y-coupler, it would be possible to use (FIG. 4) two groups of optical fibers 62, one of the groups 59 being used for supplying the exciting light for the deposit and the other group 61 being used for transmitting the fluorescent light.

Each fiber of one or other group has a split end leading to an optical system constituted by lenses 63, whose function is on the one hand to bring about the maximum concentration of the exciting light on the surface of the deposit and on the other hand to collect most of the light emitted by the fluorescent aerosol. All these ends are fastened to one another in a rigid tube 64 which, like tube 60, traverses duct 38 via a tight passage. The optical system located between the split ends of the fibers and support 40 is maintained in duct 38 by a support 65 having openings permitting the circulation of air.

Said ends of fibers 62 are homogeneously intermixed, so as to obtain a homogeneous excitation of the deposit and a homogeneous recovery of the fluorescent light.

The electronic processing means 10 serve to determine the mass concentration of the aerosol as a function of the pulses supplied by photomultiplier 50. Such means 10 are e.g. commercially available from optoelectronics companies such as Sopra or Oriel.

More specifically, said means 10 incorporate means 66 for counting the pulses supplied by the photomultiplier 50 and possibly a microcomputer system 68 connected to the counting means 66 and serving to calculate and display the sought mass concentration, as a function of the information supplied by the counting mass 66 and flow rate values supplied by flowmeter 18, as well as all the parameters corresponding to the measurement performed, in order to permit the storage, processing and editing thereof.

Advantageously, the time necessary for the measurement is fixed by a counting threshold, which thus corresponds to a given number of pulses supplied by the photomultiplier 50, so as to correspond to the optimum measurement sensitivity. This leads to a better sensitivity than with the known methods, whereof an example was given hereinbefore.

Thus, with the known method for testing filters for aerosols, the maximum sensitivity presently obtainable corresponds to a mass of approximately $10^{-10}$ gram of fluorescent material collected on a filter with a maximum flow rate of 200 liters/minute and measured in a 1 $cm^3$ ammoniacal water volume sampled in the solution of a minimum volume of 10 $cm^3$ necessary for dissolving the uranin deposited on the filter. This maximum sensitivity is obtained by taking all the precautions necessary for reducing background noise due to the filtering support and the glassware necessary for the measurement (careful washing of this glassware, measurement of the background noise level and centrifuging the solution obtained prior to the measurement).

In the embodiment of the invention shown in FIG. 1, the sensitivity is significantly improved due to the fact that the fluorescence is concentrated in a very small volume, namely the volume of the droplets deposited on the support, that the fluorescent light emitted by the deposit is collected on a solid angle of close to $2\pi$ sr and that a permanent deposit is available, which makes it possible to take advantage of an accummulation effect.

The sensitivity is further improved by carefully selecting the optical exciting and emitting filters, by using a pulsed exciting light source able to supply maximum intensity light pulses and by reducing the background noise during the detection of the fluorescent light, which can be obtained by cooling photomultiplier 50.

The device according to the invention is not limited to use with uranin. The person skilled in the art can adapt the optical elements of said device (in particular the filters of groups 56 and 58), in order to be able to use this device with some other fluorescent aerosol.

Moreover, the person skilled in the art can adapt this device to use with a liquid instead of a solid aerosol. The device can be adapted to measuring the efficiency of filters for aerosols by means of the aerosol DOP (imposed by the US measuring standard), or any other similar liquid such as DEHS (diethyl hexyl sebacate) presently proposed as a substitute for DOP due to the cancerigenic properties attributed to the latter, provided that the liquid aerosol is marked, when produced, by a fluorescent tracer (e.g. POTOMAK YELLOW for DOP) and that the saturator-condenser assembly is dimensioned so that it can be used with the vapor of the same liquid.

Furthermore, methods other than analysis by fluorimetry can be used for carrying out the concentration measurement on the aerosol deposit. Thus, it is e.g. possible to use nuclear detection means, thus permitting the determination of the volume activity of a radioactive aerosol.

In this case, deposit 43 (FIG. 5), which is the homolog of deposit 42 and which can then emit beta or gamma radiation for example, is formed on one face of a support 41, which is the homolog of support 40 and which is transparent to said radiation, an appropriate detector 45 being placed facing the other face of support 41. In the case where the radiation is of the beta type, deposit 43 can be directly formed on the intake face of the corresponding appropriate detector, this also being possible when the radiation is of the alpha or gamma type. The appropriate detector 45 supplies information to appropriate processing means 47, making it possible to obtain information of the radioactive aerosol in question in the air.

Finally, the applications of the invention are not limited to measuring the efficiency of filters for aerosols. Thus, the present invention also applies to the tracing, by means of uranin or another fluorescent aerosol, of gaseous flows able to carry noxious (e.g. radioactive) aerosols within ventilated rooms or outside installations representing risks for their environment.

We claim:

1. A device for measuring the content of an aerosol in a gas charged with said aerosol on the basis of a sampling of said aerosol charged gas, said device comprising enlargement means able to condense, on the thus sample aerosol, a vapor of a liquid, so as to obtain droplets of a solution of the aerosol in the liquid, impaction means, able to project said droplets onto a support provided for collecting at least one known fraction of these droplets, means for the continuous analysis of the thus collected droplets, said analysis means being specific to the aerosol whose content is to be measured and able to supply information relative to said content and electronic means for processing the information and able to determine the content on the basis of said information.

2. A device according to claim 1, wherein the aerosol is fluorescent and the analysis means comprise optoelectronic means for exciting and detecting fluorescence and able to supply said information.

3. A device according to claim 2, wherein the optoelectronic means comprise means for forming a fluorescence exciting light beams, means for detecting a fluorescent light resulting from the excitation and fiber optics means able to transmit said exciting light beam to the collected droplets and to transmit the fluorescent light to the detection means.

4. A device according to claim 3, wherein the support is transparent to the exciting beam and to the fluorescent light, the droplets are collected on one face of the support, the fiber optics means comprise two groups of optical fibers, each optical fiber having one end positioned facing the other face of said support, in that the ends of the optical fibers, placed facing the other face of the support, are intermixed and the two groups are respectively provided for transmitting the exciting beam and the fluorescent light.

5. A device according to claim 1, wherein the aerosol is an emitter of alpha, beta or gamma radiation, and the analysis means incorporate means for detecting this radiation and able to supply information.

6. A device according to claim 1, wherein the aerosol is solid.

7. A device according to claim 6, wherein the aerosol is sodium-containing fluorescein.

8. A device according to claim 1, wherein the aerosol is liquid.

9. A device according to claim 1, wherein the aerosol is less than 0.5 $\mu$m in size.

* * * * *